United States Patent

Devries et al.

[11] Patent Number: 5,916,902
[45] Date of Patent: Jun. 29, 1999

[54] PROCESSES AND INTERMEDIATES FOR PREPARING 5, 7-DIHYDRO-3-[2-(1-BENZYLPIPERIDIN-4-YL)ETHYL-]6H-PYRROLO-[4, 5-F]-1, 2-BENZISOXAZOL-6-ONE

[75] Inventors: Keith M. Devries, Chester; Anabella Villalobos, Niantic, both of Conn.

[73] Assignee: Pfizer Inc., NY, N.Y.

[21] Appl. No.: 08/836,114

[22] PCT Filed: Sep. 13, 1995

[86] PCT No.: PCT/IB95/00755

§ 371 Date: Apr. 16, 1997

§ 102(e) Date: Apr. 16, 1997

[87] PCT Pub. No.: WO96/13505

PCT Pub. Date: May 9, 1996

[51] Int. Cl.$^6$ ............. A61K 31/445; C07D 401/06; C07D 401/12
[52] U.S. Cl. ............. 514/321; 514/322; 514/323; 546/197; 546/198; 546/199; 546/201
[58] Field of Search ................. 514/321, 322, 514/323; 546/197, 198, 199, 201

[56] References Cited

U.S. PATENT DOCUMENTS

| | | | |
|---|---|---|---|
| 5,532,240 | 7/1996 | Nakao et al. | 514/254 |
| 5,538,984 | 7/1996 | Villalobos et al. | 514/322 |

FOREIGN PATENT DOCUMENTS

| | | |
|---|---|---|
| 92/17475 | 10/1992 | WIPO . |
| 93/04063 | 3/1993 | WIPO . |

OTHER PUBLICATIONS

McOmie "Protective groups in organic chemistry" Plen. Press, p. 109–120 1973.

Primary Examiner—Ceila Chang
Attorney, Agent, or Firm—Peter C. Richardson; Paul H. Ginsburg; Lorraine B. Ling

[57] ABSTRACT

This invention relates to a process for preparing the compound having the formula

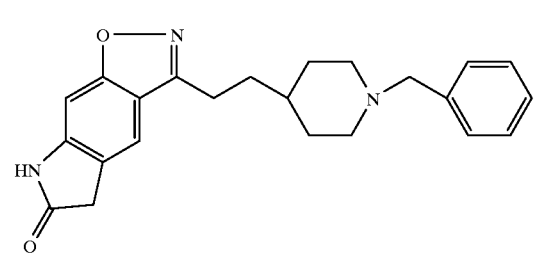

which comprises i) heating the compound of formula

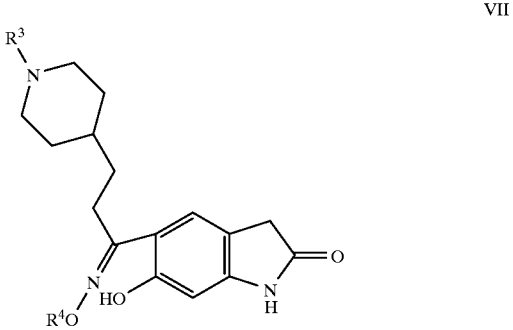

wherein $R^3$ is $R^4$ or benzyl and $R^4$ is $R^5C(=O)$, $R^5C(=O)$ or $R^5SO_2$ wherein $R^5$ is $(C_1–C_6)$alkyl or $(C_6–C_{10})$aryl$(C_1–C_6)$alkyl;

at an elevated temperature in the presence of a base with the proviso that when $R^3$ in the resultant product is $R^4$ said product is ii) further treated with an aqueous mineral acid at an elevated temperature followed by iii) treatment of the product of ii) with a) a benzylating agent in the presence of a base or b) benzaldohyde in the presence of a reducing agent and an acid.

21 Claims, No Drawings

PROCESSES AND INTERMEDIATES FOR PREPARING 5, 7-DIHYDRO-3-[2-(1-BENZYLPIPERIDIN-4-YL)ETHYL-] 6H-PYRROLO-[4, 5-F]-1, 2-BENZISOXAZOL-6-ONE

This application is a 371 of PCT/IB95/00755 filed Sep. 13, 1995.

BACKGROUND OF THE INVENTION

The present invention relates to the compound of the formula I, below, and pharmaceutically acceptable salts and pro drugs thereof. More particularly, it relates to processes and intermediates for use in the preparation of the compound of formula I.

The compounds of formula I are cholinesterase inhibitors and are useful in enhancing memory in patients suffering from dementia and Alzheimer's disease.

The compound of formula I is disclosed in co-pending U.S. patent application Ser. No. 08/127,847 (assigned to the Assignee of this application), incorporated herein by reference.

Alzheimer's disease is associated with degeneration of cholinergic neurons in the basal forebrain that play a fundamental role in cognitive functions, including memory. Becker et al., *Drug Development Research*, 12, 163–195 (1988). As a result of such degeneration, patients suffering from the disease exhibit a marked reduction in acetylcholine synthesis, choline acetyltransferase activity, acetylcholinesterase activity and choline uptake.

It is known that acetylcholinesterase inhibitors are effective in enhancing cholinergic activity and useful in improving the memory of Alzheimer's patients. By inhibiting the acetylcholinesterase enzyme, these compounds increase the level of the neurotransmitter acetylcholine in the brain and thus enhance memory. Becker et al., supra, report that behavioral changes following cholinesterase inhibition appear to coincide with predicted peak levels of acetylcholine in the brain. They also discuss the efficacy of the three known acetylcholinesterase inhibitors physostigmine, metrifonate, and tetrahydroaminoacridine.

All documents cited herein, including the foregoing, are incorporated herein in their entireties.

SUMMARY OF THE INVENTION

The present invention relates to processes and intermediates, and processes for the preparation of said intermediates, for the preparation of the compound of the formula

I

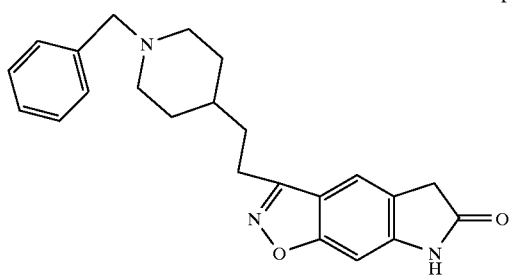

More particularly, the invention relates to a process for the preparation of the compound of formula I which comprises a) treating a compound of the formula

V

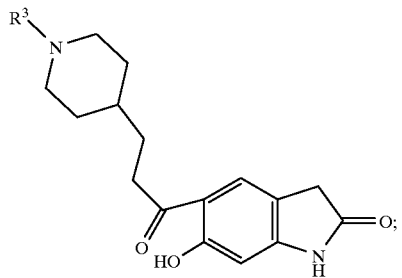

wherein $R^3$ is benzyl or $R^4$, wherein $R^4$ is selected from $R^5$—C(=O)—, $R^5SO_2$— and $R^5OC(=O)$— and $R^5$ is $(C_1-C_6)$alkyl, $(C_6-C_{10})$aryl or aryl$(C_1-C_6)$alkyl; with hydroxylamine to form the compound of formula

VI

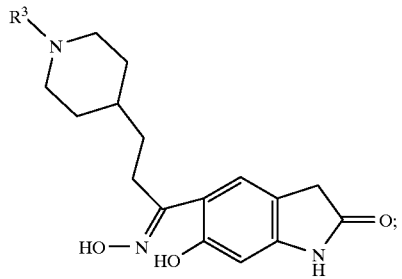

wherein $R^3$ is as defined above;

b) treating the compound of formula VI with an acylating agent selected from the group comprising acyl or aroyl anhydrides, halides and esters; or a sulfonating agent selected from the group comprising alkyl, aryl or aralkyl sulfonyl halides and anhydrides, and halides of groups of the formula $R^5OC(=O)$— to form the compound of formula

VII wherein $R^3$ and $R^4$ are as defined above;

c) treating the compound of formula VII with a base at an elevated temperature, to form i) when R³ is

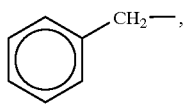

the compound of formula I; or ii) when R³ is not benzyl, the compound of the formula

VIII

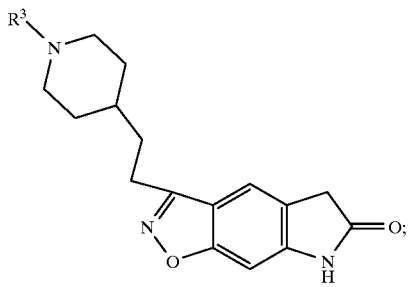

2) treating the compound of formula VIII, wherein R³ is not benzyl with an aqueous mineral acid at an elevated temperature and then with a base to form the compound of formula

IX

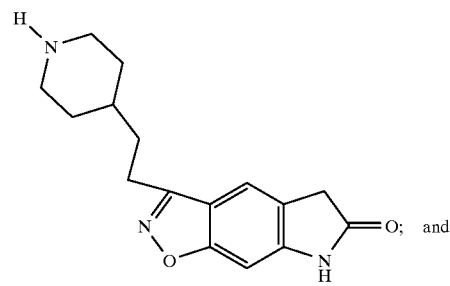

3) treating the compound of formula IX with a benzylating agent in the presence of a base to form the compound of formula I. A preferred benzylating agent is a benzyl halide, preferably benzyl bromide, and a preferred base is triethanolamine This invention also relates to compounds of the formula

II

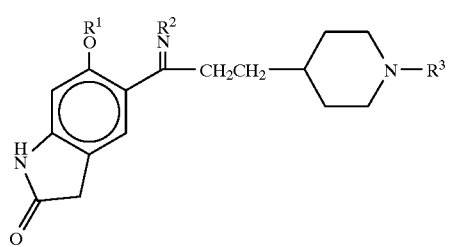

$R^1$ is H and $R^2$ is OH or $OR^4$ wherein $R^4$ is $4R^5C(=O)$, $R^5OC(=O)$ or $R^5SO_2$ wherein $R^5$ is $(C_1-C_6)$alkyl, $(C_6-C_{10})$aryl or $(C_6-C_{10})$aryl$(C_1-C_6)$alkyl; or $R^1$ and $R^2$ together form a single bond, $R^3$ is $R^4$ or benzyl with the proviso that when $R^1$ and $R^2$ together form a single bond, $R^3$ is not benzyl. These compounds are useful as intermediates in the synthesis of compounds of the formula I.

More specifically, this invention relates to compounds of the formulae

IIA

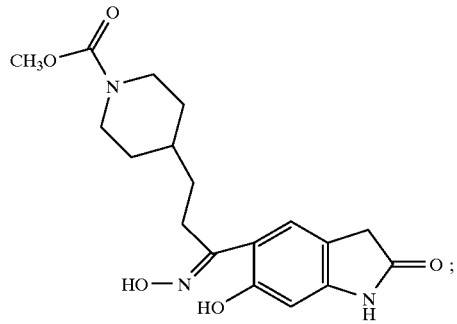

IIB

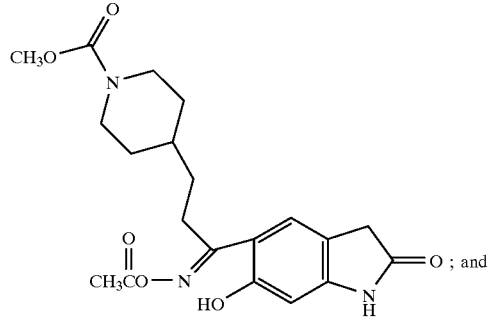

IIC

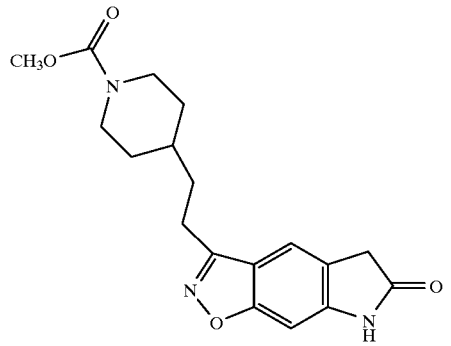

DETAILED DESCRIPTION OF THE INVENTION

The preparation of the compound of formula I, and certain of the starting materials used therein is illustrated in the following reaction schemes. Except where otherwise stated, in the reaction schemes and discussion that follow, $R^1$, $R^2$, $R^3$, $R^4$, $R^6$, $R^7$ and $R^8$ and structures I, II, IIA, IIB and IIC are defined as above.

All articles, books, patents and patent applications cited in the following discussion are incorporated herein by reference.

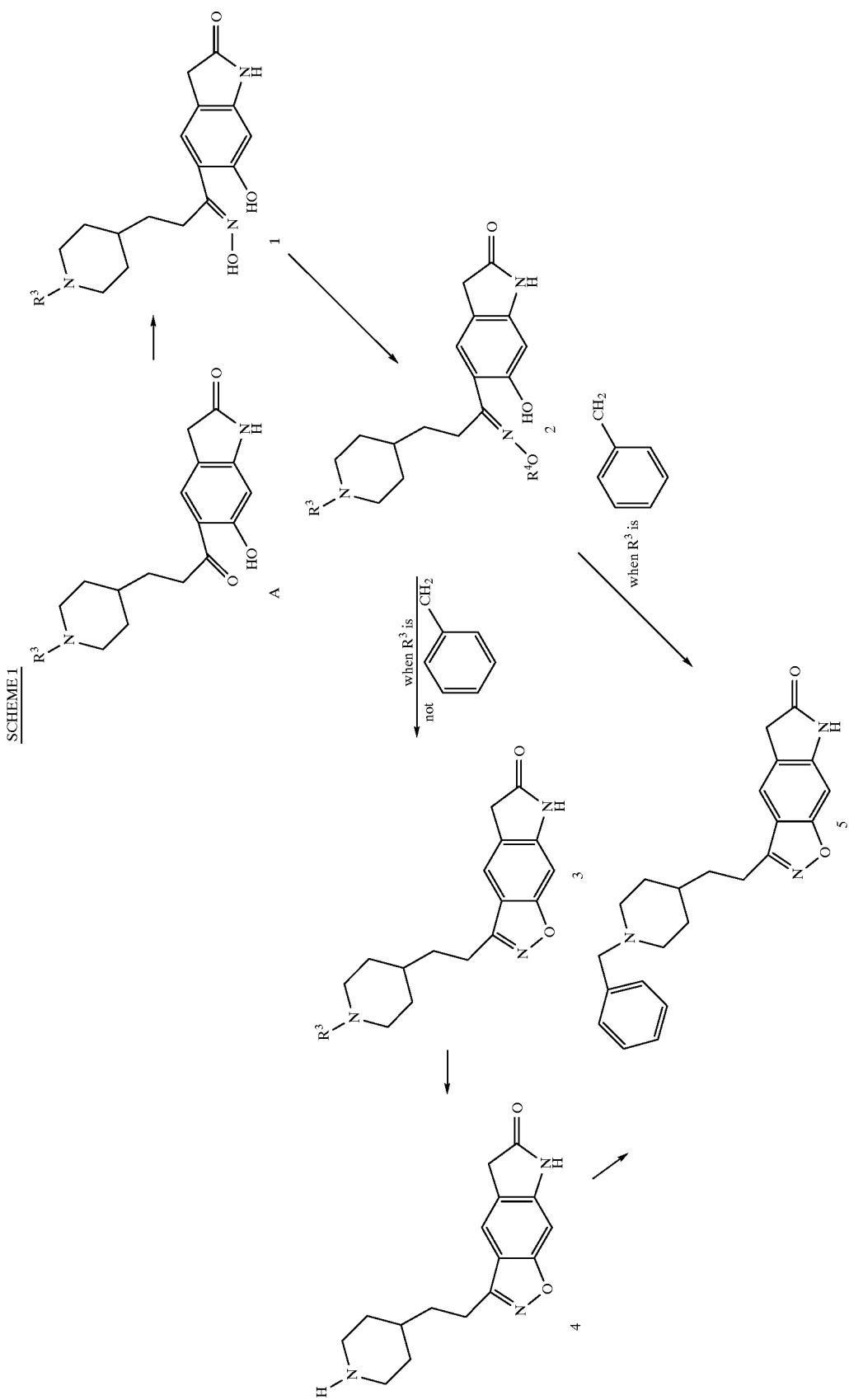

Compound A is converted to compound 1 by reaction with an hydroxylamine salt, preferably the hydrochloride, in the presence of an appropriate base such as potassium or sodium hydroxide, sodium acetate or pyridine, preferably aqueous potassium hydroxide or aqueous sodium acetate, in a polar solvent such as methanol, ethanol, water or mixtures thereof, preferably a mixture of ethanol and water, at a temperature from about room temperature to about 120° C., preferably about 80° C. The starting material A can be prepared by methods known in the art.

Compound 1 is then converted to compound 2 by treatment with an appropriate acylating or sulfonating agent, such as an anhydride, halide or ester, or a carbamyl halide in a polar solvent, such as those described above, or ethers such as tetrahydrofuran (THF). Temperatures for this reaction may range from about room temperature to the reflux temperature of the solvent. Preferably the reaction is carried out in THF at about room temperature.

Compound 3 may be prepared by heating neat compound 2 at a temperature from about 125° C. to about 200° C. under atmospheric pressure or reduced pressure (e.g., from about 0.01 mm Hg ($1.33 \times 10^{-5}$ bars) to about 760 mm Hg(1.01 bars)). Ring closure is preferably accomplished by heating the compound 2 at reflux in an appropriate base such as pyridine or 2,6-lutidine or by heating at a temperature of about 130° C. in a polar solvent such as dimethylformamide (DMF), dimethylsulfoxide (DMSO) or THF in the presence of several equivalents of an appropriate base such as pyridine or 2,6-lutidine. Preferably the reaction is carried out in refluxing THF and the base is 2,6-lutidine.

Alternatively, compound 3 may be prepared from compound 1 directly by reaction of compound 1 with an acyl or sulfonyl chloride such as oxalyl or thionyl chloride in the presence of an aromatic amine such as pyridine (See Kalkote et al., *Aust. J. Chem.* 1977, 30, 1847). Suitable solvents include polar solvents such as diethyl ether or THF. Temperatures can range from about 0° C. to about room temperature. Another method of closure involves treatment of compound 1 with one or less equivalents of a base such as potassium hydroxide in a polar solvent such as methanol at temperatures ranging from about room temperature to about 100° C. (Crabbe et al., *J. Chem. Soc. Perkin Trans. I*, 1973, 2220).

When $R^3$ is $C_6H_5CH_2$— compound 3 is the same as compound 5.

When $R^3$ is a nitrogen protecting group it can be removed from compound 3 to form compound 4 by methods known to those skilled in the art. For example, when $R^3$ is $(CH_3)_3CO(C=O)$—(BOC) or another carbamate, it can be removed with an acid such as hydrogen bromide (gas or aqueous), hydrogen chloride (gas or aqueous) or trifluoroacetic acid. In the case of trifluoroacetic acid, a t-butyl cation scavenger such as thioanisole may be added. When an acid is used as the deprotecting agent an acid addition salt of compound 4 is produced rather than the free base of such compound 4. Appropriate solvents include non-polar solvents such as methylene chloride, as well as polar solvents such as diethyl ether, ethyl acetate, dioxane, alcohols (e.g. methanol or ethanol) and water. Temperatures may range from about −20° C. to about the reflux temperature of the solvent. Where the protecting group is an acyl or carbamate group the preferred deprotecting composition is 3–12N, preferably 6 N, HCl (aqueous) and the temperature is from about room temperature to about reflux, preferably from about 80 to about 90° C.

Alternatively, when $R^3$ is BOC, it can be removed with a trialkylsilyltrifluoromethanesulfonate derivative such as trimethylsilyl-, triethylsilyl-, or t-butyldimethylsilyl-trifluoromethanesulfonate in the presence of an aromatic or tertiary amine base such as 2,6-lutidine or triethylamine. Appropriate solvents for this reaction include nonpolar solvents such as methylene chloride and polar aprotic solvents such as THF, diethyl ether or DMF. Temperatures may range from about −20° C. to room temperature. It is preferable to use trimethylsilyltrifluoromethane-sulfonate and 2,6-lutidine in methylene chloride at a temperature from about 0° C. to about room temperature.

Compound 4 is preferably converted to compound 5 by treatment with a benzylating agent, such as a benzyl halide, in the presence of a base. A preferred benzylating agent is benzyl bromide and a preferred base is triethanolamine. Solvents for use in this reaction include chlorinated hydrocarbons, as described above, in ($C_1$-$C_6$)alkanoic acids, ($C_1$–$C_6$)alkanols, ethers, such as diethylether, cyclic ethers, such as tetrahydrofuran (THF) and dioxane and mixtures thereof. The preferred solvent is THF.

Compound 4 may also be converted to compound 5 by reductive amination with benzaldehyde, in an inert solvent, as described above in the presence of a reducing agent.

Useful reducing agents include borohydrides, such as those of the alkali metals, $NaHB(CN)_3$ and triacetoxyborohydride; and borane complexes such as those with pyridine and triethylamine. A preferred solvent is $CH_2Cl_2$/acetic acid and a preferred reducing agent is triacetoxyborohydride.

In each of the above reactions, unless otherwise indicated, pressure is not critical. Pressures in the range of about 0.5–3 atm (0.5–3 bars) are suitable, and ambient pressure (generally, about one atmosphere) is preferred as a matter of convenience. Also, for those reactions where the preferred temperature varies with the particular compounds reacted, no preferred temperature is stated. For such reactions, preferred temperatures for particular reactants may be determined by monitoring the reaction using thin layer chromatography.

The compounds of formula I and their pharmaceutically acceptable acid addition salts (hereinafter referred to as the "active compounds") may be administered to a patient by various methods, for example, orally as capsules or tablets, parentally as a patch, sterile solution or suspension, and in some cases, intravenously in the form of a solution. The free base compounds of the invention may be formulated and administered in the form of their pharmaceutically acceptable acid addition salts.

The daily dose of the active compounds is generally in the range of from about 0.005 to about 300 mg/day, optionally from about 0.01 to 300 mg/day, and preferably from about 0.01 to about 30 mg/day for the average adult human, and may be administered in single or divided doses.

When incorporated into a solution or suspension, for parenteral administration, the active compounds are present in a concentration of at least about 0.0005 weight percent, and preferably between about 0.001 to about 30 weight percent (based on the total weight of the unit). The parenteral dosage unit typically contains between about 0.5 to about 100 mg of active compound(s).

The active compounds may be administered orally with an inert diluent or an edible carrier, or they may be enclosed in gelatin capsules or compressed into tablets. Such preparations should contain at least about 0.0005% of active compound(s), but the concentration may vary depending upon the particular form and may be from about 0.001 to about 30 weight percent (based on the total weight of the unit). The oral dosage unit typically contains between about 0.01 mg to about 30 mg of active compound.

The cholinesterase inhibiting activity of the active compounds may be determined by a number of standard biological or pharmacological tests. One such procedure for determining cholinesterase inhibition is described by Ellman et al. in "*A New and Rapid Colorimetric Determination of Acetylcholinesterase Activity*", Biochem. Pharm. 1, 88, (1961).

The present invention is illustrated by the following examples. It will be understood, however, that the invention is not limited to the specific details of these examples. Melting points are uncorrected. Proton nuclear magnetic resonance spectra ($^1$H NMR) were measured for solutions in deuterochloroform ($CDCl_3$) except where otherwise noted and peak positions are expressed in parts per million (ppm). The peak shapes are denoted as follows: s, singlet; d, doublet; t, triplet; q, quartet; m, multiplet; br, broad. Frequencies (J) are expressed in Hertz.

EXAMPLE 1

Preparation of 5-(3[N-(Methoxycarbonyl)piperidin-4-yl]proprionyl)-1,3-dihydro-6-hydroxy-2H-indol-2-one a) Preparation of 3-pyridin-4ylpropen-2-oic acid To a solution of pyridin-4-ylcarboxaldehyde (100 g, 0.93 mol) in 100 mL of pyridine (1.0 equiv.) was added malonic acid (100 g, 0.96 mol) at 90° C. After $CO_2$ evolution subsided, the reaction slurry was diluted with methanol. The title compound was isolated as a white solid by filtration.

$^1$H NMR ($CH_3CO_2H$-$d_4$)δ11.70 (s, 1H), 8.85 (d, 2H), 7.95 (d, 2H), 7.80 (d, 1H), 6.90 (d, 1H).

b) Preparation of 3-piperidin4-ylpropanoic acid

The product of step a) was dissolved in 150 mL of 2 N HCl and treated with 10 weight % of 5% Rh—C and hydrogen until hydrogen gas uptake ceased. The catalyst was removed by filtration and the resulting solution used directly in the next step.

$^1$H NMR ($D_2O$) δ3.25 (m, 2H), 2.80 (m, 2H), 225 (t, 2H), 1.75 (m, 2H), 1.50-1.10 (m, 5H). FABMS (M+1)$^+$=157 c) Preparation of 3-[N-(methoxycarbonyl)-piperidin4-yl] proprionic acid

The solution from step b) was brought to pH 12 with aqueous potassium hydroxide. To this solution was added 21 mL methyl chloroformate (0.27 mol). After the reaction was complete, the solution was brought to pH 1 with 6 N HCl and extracted with dichloromethane. The organic layer was dried with sodium sulfate and the dichloromethane displaced with isopropyl ether. The product was isolated as a solid by filtration. Yield 39 gm, 84%. M.p. 89–90° C.

$^1$H NMR ($CDCl_3$) δ4.10 (m, 2H), 3.65 (s, 3H), 2.70 (m, 2H), 2.35 (t, 2H), 1.80-1.10 (m, 7H).

d) Preparation of 3-[N-(methoxycarbonyl)-piperidin4-yl] proprionyl chloride

To a solution of 49.5 gm (0.23 mol) of the compound of step c), in dichloromethane, was added 0.25 mL of dimethylformamide and 21 mL of oxalyl chloride (0.25 mol). After gas evolution subsided, formation of the title compound was complete. The resulting solution was used directly into the next step.

e) The solution from step d), comprising 1.5 equiv of the title compound thereof, was added to a slurry of 25 gm (0.15 mol) of 6-methoxyindol-2-one and 102 gm (0.77 mol) of aluminum trichloride in 625 mL dichloromethane. After 2 hours the reaction was complete. The reaction was quenched with water and the product partitioned between pH 1 aqueous HCl and dichloromethane. The organic layer was separated, dried with sodium sulfate, and the dichloromethane displaced with isopropyl ether. The title compound of this Example was isolated as a solid by filtration. Yield 49 gm, 94%. M.p. 199–200° C.

$^1$H NMR ($CDCl_3$) δ13.10 (s, 1H), 8.80 (s, 1H), 7.55 (s, 1H), 6.50 (s, 1H), 4.15 (m, 2H), 3.70 (s, 3H) 3.50 (s, 2H), 2.95 (t, 2H) 2.75 (m, 2H), 1.85-1.15 (m, 7H). FABMS (M+1)$^{30}$=346.

EXAMPLE 2

Preparation of 5-(3-[N-(Methoxycarbonyl)piperidin-4-yl]proprionyl)-1,3-dihydro-6-hydroxy-2H-indol-2-one, 5-oxime A slurry of 6.0 gm (17 mmol) of the title compound of Example 1 in 4:1 ethanol/water was treated with 3.6 gm (52 mmol) of hydroxylamine hydrochloride and sodium acetate (4.3 gm, 52 mmol). The slurry was stirred at 80° C. overnight, at which time the reaction was complete. The ethanol was removed in vacuo and the title compound was isolated as a solid by filtration. Yield 5.3 gm, 86%. M.p. 247–248° C.

$^1$H NMR ($CDCl_3$+DMSO-$d_6$) δ12.10 (s, 1H), 10.95 (s, 1H), 10.30 (s, 1H), 7.60 (s, 1H), 6.30 9s, 1h), 4.00 (m, 2H), 3.60 (s, 2H), 2.80-2.60 (m, 4H), 1.80-1.00 (m, 7H). FABMS (M+1)$^+$=361

EXAMPLE 3

Preparation of 5-(3-[N-(Methoxycarbonyl)piperidin-4-yl]proprionyl)-1,3-dihydro-6-hydroxy-2H-indol-2-one, 5-oxime acetate A slurry of 5.2 gm (14 mmol) of the title compound of Example 2 in 100 mL tetrahydrofuran was treated with 1.2 gm (14 mmol) sodium acetate and 1.4 mL (15 mmol) acetic anhydride and stirred overnight at room temperature. The title compound was isolated from the crude reaction mixture, as a solid, by filtration. Yield 5.3 gm, 92%. M.p.= 139–140° C.

$^1$H NMR ($CDCl_3$) δ11.80 (s, 1H), 8.15 (s, 1H), 7.20 (s, 1H), 6.55 (s, 1H), 4.20 (m, 2H), 3.70 (s, 3H (s, 2H), 2.95-270 (m, 4H), 2.225 (s, 3H), 1.95-1.10 (m, 7H). FABMS (M+Na)$^+$=426

EXAMPLE 4

Preparation of 5.7-Dihydro-3-(2-[N-(methoxycarbonyl)-piperidin-4-yl]ethyl)-6H-pyrrolo[4.5-f]-1,2-benzisoxazol-6-one A slurry of 3.6 gm (8.8 mmol) of the title compound of Example 3 in 50 mL tetrahydrofuran containing 3.1 mL (26 mmol) 2,6-lutidine was heated at 65° C. overnight. The solution was then cooled to 0° C. and the title compound precipitated upon addition of isopropyl ether. The title compound was isolated by filtration. Yield 2.2 gm, 72%.

$^1$H NMR ($CDCl_3$ δ8.70 (s, 1H), 7.45 (s, 1H), 7.05 (s, 1H), 4.15 (m, 2H), 3.70 (s, 3H), 3.60 (s, 2H), 3.00 (t, 2H), 2.75 (m, 2H), 1.85-1.05 (m, 7H). FABMS (M+1)$^+$=343

EXAMPLE 5

Preparation of 5,7-Dihydro-3-[2-[1-benzylpiperidin-4yl]ethyl]-6H-pyrrolo[4,5-f]-1.2-benzisoxazol-6-one a) A slurry of 0.65 gm (1.9 mmol) of the title compound of Example 4 in 6 N HCl was heated at 100° C.

overnight. The solution was then cooled to 0° C. and the product precipitated upon basification to pH 10 with aqueous NaOH. The product was isolated as a solid by filtration. Yield 420 mg, 78%. M.p. 248–9° C.

$^1$H NMR (CDCl$_3$+CD$_3$OD) δ7.70 (s, 1H), 7.00 (s, 1H), 3.60 (s, 2H), 3.05 (m, 2H), 2.95 (t, 3H), 2.55 (m, 2H), 1.85-.10 (m, 7H). FABMS (M+1)$^+$=285 b) i) A slurry of 1.44 gm of the product of step a) (5.1 mmol) in 50 mL of THF was treated with 0.61 mL of benzyl bromide (5.1 mmol) and 0.76 gm of triethanolamine (5.1 mmol). The reaction mixture was heated overnight at 65° C. and then filtered. The filtrate was evaporated and the resultant solid recrystallized from 20 mL of hot ethyl acetate. Upon cooling, the title compound was isolated as a solid by filtration (1.40 gm,74%). M.p. 118–119° C.

$^1$H NMR (CDCl$_3$) δ9.05 (s, 1H), 7.45 (s, 1H), 7.20-7.40 (m, 5H), 7.00 (s, 1H), 3.65 (s, 2H), 3.60 (s, 2H),3.00-2.85 (m, 4H), 2.05-1.25 (m, 9H). FABMS (M+1)$^+$=375.

ii) A slurry of 1.44 gm (5.1 mmol) of the product of step a), in dichloroethane, was treated with benzaldehyde (1.5 equiv.), acetic acid (1.0 equiv.), and triacetoxyborohydride (3.0 equiv.) and stirred overnight at room temperature. The reaction was quenched by addition of aqueous sodium bicarbonate and then diluted with dichloromethane. The organic layer was separated, dried with sodium sulfate, and concentrated in vacuo. The crude solid was recrystallized from ethyl acetate to provide the title compound.

We claim:

1. A process for preparing the compound having the formula

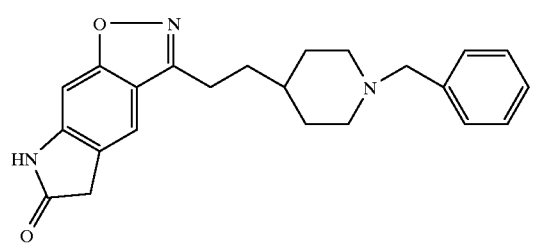

I which comprises i) heating a compound of formula

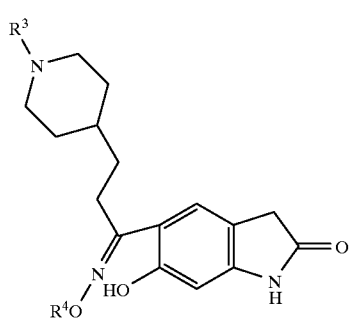

VII wherein R$^3$ is R$^4$ or benzyl and R$^4$ is selected from R$^5$—C(=O)—, R$^5$SO$_2$— and R$^5$OC(=O)— and R$^5$ is (C$_1$–C$_6$) alkyl, (C$_6$–C$_{10}$)aryl or aryl(C$_1$–C$_6$)alkyl; at an elevated temperature in the presence of a base with the proviso that when R$^3$ in the resultant product is R$^4$ said product is ii) further treated with an aqueous mineral acid at an elevated temperature followed by iii) treatment of the product of ii) with a) a benzylating agent in the presence of a base or b) benzaldehyde in the presence of a reducing agent and an acid.

2. The process of claim 1 step ii) wherein said acid is 3–12 N HCl and said temperature is from about room temperature to about reflux.

3. The process of claim 2 wherein said acid is 6N HCl and said temperature is from about 80 to about 90° C.

4. The process of claim 1 wherein said benzylating agent is a benzyl halide.

5. The process of claim 4 wherein said benzyl halide is benzyl bromide.

6. The process of claim 1 wherein the base of step iii) a) is triethanolamine.

7. The process of claim 1 wherein the base of step i) is 2,6-lutidine.

8. The process of claim 1 step iii) b) wherein said reducing agent is triacetoxyborohydride and said acid is acetic acid.

9. The process of claim 1 wherein the compound of formula VII is prepared by treating the compound of formula

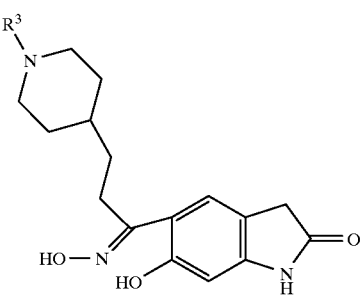

VI wherein R$^3$ is as defined above;
with an acylating, carbamylating or sulfonating agent in the presence of a base.

10. The process of claim 9 wherein said acylating agent is acetic anhydride and said base is sodium acetate.

11. The process of claim 9 wherein the compound of formula VI is prepared by treating the compound of formula

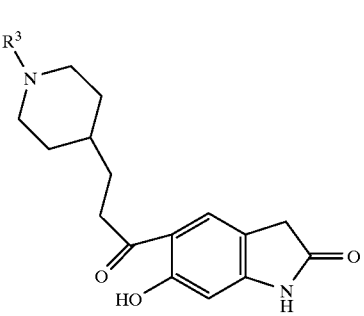

V wherein R$^3$ is as defined above, with hydroxylamine salt in the presence of a weak base.

12. The process of claim 11 wherein said salt is the hydrochloride and said weak base is sodium acetate.

13. A process for preparing a compound having the formula

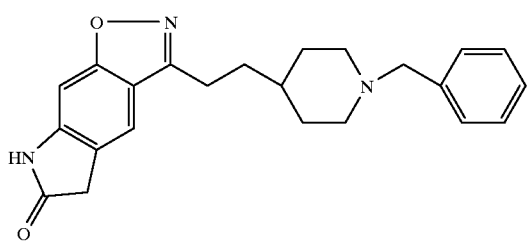

which comprises the steps of
a) treating a compound of the formula

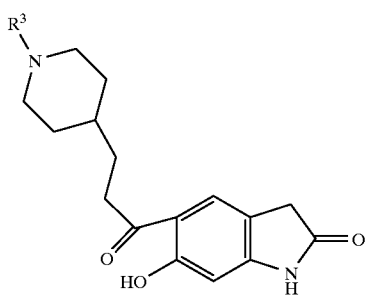

wherein R³ is as defined above;
with a hydroxylamine salt in the presence of a weak base to form the compound of formula

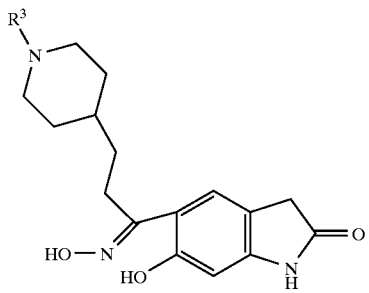

wherein R³ is as defined above;
b) treating the compound of formula VI with an acylating, carbamylating or sulfonating agent in the presence of a base to form the compound of the formula

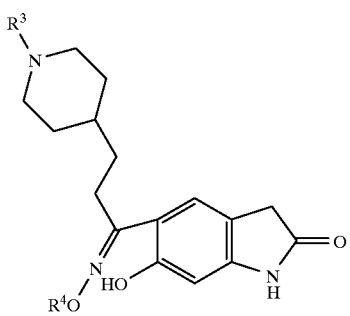

wherein R³ and R⁴ are as defined above; and c) treating the compound of formula VII with a base at an elevated temperature to form
i) when R³ is

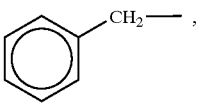

the compound of formula I; or
ii) when R³ is R⁴ a product of the formula

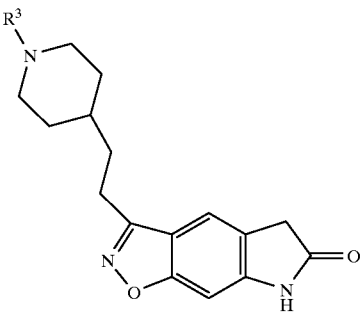

wherein R³ is as defined above;
iii) treating the compound of formula VIII with an aqueous mineral acid at an elevated temperature and then with a base to form the compound of formula

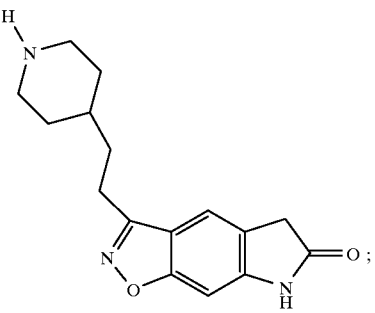

and
iv) a) treating the compound of formula IX with a benzylating agent in the presence of a base or b) benzaldehyde in the presence of a reducing agent and an acid to form the compound of formula I.

14. A compound of the formula

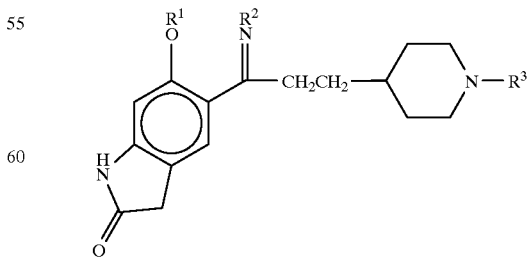

R¹ is H and R² is OH or OR⁴ wherein R⁴ is R⁵C(=O), R⁵OC(=O) or R⁵SO₂ wherein R⁵ is (C₁–C₆)alkyl, (C₆–C₁₀)

aryl or $(C_6-C_{10})$aryl$(C_1-C_6)$alkyl; or $R^1$ and $R^2$ together form a single bond, $R^3$ is $R^4$ or benzyl with the proviso that when $R^1$ and $R^2$ together form a single bond $R^3$ is not benzyl.

15. The compound of claim 14 wherein $R^1$ is hydrogen and $R^2$ is hydroxyl or $OR^4$ and $R^3$ and $R^4$ are as defined above.

16. The compound of claim 15 wherein $R^2$ is OH.

17. The compound of claim 15 wherein $R^2$ is $OR^4$ and $R^4$ is as defined above.

18. The compound of claim 14 wherein $R^1$ and $R^2$ together form a single bond.

19. The compound of claim 14 wherein $R^3$ is $R^4$ and $R^4$ is as defined above.

20. The process of claim 13 step c) iv) wherein said benzylating agent is benzyl bromide and said base is triethanolamine.

21. The process of claim 20 step b) wherein said base is 2,6-lutidine.

* * * * *